United States Patent [19]

Whitehead

[11] Patent Number: 4,508,531
[45] Date of Patent: Apr. 2, 1985

[54] CONVOLUTELY WOUND PAPER TAMPON TUBE

[75] Inventor: Howard A. Whitehead, Outagamie County, Wis.

[73] Assignee: Kimberly-Clark Corporation, Neenah, Wis.

[21] Appl. No.: 446,838

[22] Filed: Dec. 6, 1982

[51] Int. Cl.³ .............................................. A61F 15/00
[52] U.S. Cl. ....................................... 604/14; 604/904
[58] Field of Search .................... 604/14, 15, 904, 16, 604/17, 18, 19

[56] References Cited

U.S. PATENT DOCUMENTS

| | | | |
|---|---|---|---|
| 3,581,744 | 6/1971 | Voss et al. | 604/14 |
| 3,954,104 | 5/1976 | Kraskin et al. | 604/15 |
| 4,273,125 | 6/1981 | Sakurai | 604/16 |
| 4,412,833 | 11/1983 | Wiegner et al. | 604/14 |

Primary Examiner—John D. Yasko
Attorney, Agent, or Firm—Howard Olevsky; R. J. Peters; J. P. O'Shaughnessy

[57] ABSTRACT

A flexible convolutely wound paper tampon tube is provided in which a thermoplastic coating on either the interior or the exterior portion of the tube is present in an amount to maintain the tube configuration.

1 Claim, 3 Drawing Figures

CONVOLUTELY WOUND PAPER TAMPON TUBE

FIELD OF THE INVENTION

The subject invention relates to a cardboard tube particularly useful for the insertion of a tampon and a process for making the same.

BACKGROUND OF THE INVENTION

Tampons conventionally sold in the United States employ means for insertion of the tampon pledget into the user's vagina. These means generally are in two parts with the outer part being a tube with an inner diameter slightly greater than the outer diameter of the tampon pledget. The second part of a tampon inserter means is some time of plunger which operates in cooperation with the tube to expel the pledget. The tubes are generally made of paper products such as cardboard or thermoplastic. Further, thermoplastic tubes generally have an insertion end which forms a hemispherical profile around the leading edge of the tampon to protect it and maintain its integrity during insertion. Commercially available tampons utilizing cardboard tubes, however, generally do not have this type of closure, but rather the leading edge of the tampon extends beyond the tube end. Both thermoplastic and paper derived tubes can be made with a reduced diameter base which can be used for gripping or to better maintain the plunger used for expulsion, or for both purposes.

The ideal tampon tube should be inexpensive, simple to make, easily disposable, attractive and hygienic. Both molded plastic and paper inserter tubes have not been completely satisfactory in meeting these desirable attributes. Tubes which are molded from the thermoplastics are neither water dispersible or flushable. Furthermore, the relative cost of thermoplastic is substantially greater than tubes which are made from paper or paper products. In addition, thermoplastic molded tubes having a hemispherical shaped leading edge comprising individual arcuate shaped lobes are extremely difficult to mold without providing lobes having sharp edges or flashing, i.e., irregularly shaped burrs of plastic. Such tubes could provide problems when being withdrawn from the vagina. Paper tubes, on the other hand, also have problems. Commercially available cardboard tubes for tampons are generally spirally wound and open at the leading edge which may result in a fiber slough when the tampon is inserted. The only known paper tubes with shaped tips are spirally wound with the shaping of the tips being accomplished by crushing, deforming and pleating the formed tube, or alternatively, by cutting triangular shaped petals in a preformed tube. Both of these methods for forming a tube which covers the insertion edge of the pledget are complex and in the case of crushing, deforming and pleating, expulsion of the tampon is extremely difficult. If a paper based tampon tube having a plurality or arcuate lobes with a hemispherical profile is desired, and the tubes are cut from a flat tampon blank, spiral winding will produce "ghosting", i.e., an overlap of the individual lobe segments due to the spiral winding. Attempts to produce such a leading edge with a spirally wound tube, therefore, are best performed after the tube is formed which is substantially more difficult. As can be seen from the previous discussion, while a paper based tampon tube with a hemispherical leading edge to cover the tampon is highly desirable from the standpoint of material cost and disposability, the difficulties in forming such a tube have inhibited their practical application. The tampon tube of this invention buy employing convolute winding and a thermoplastic coating overcomes many of the difficulties associated with paper-based tampon tube manufacture.

An approach which is currently preferred is to employ a water soluble or water dispersible thermoplastic binder which would aid in disposal of the applicator. If such a composition was used as the only thermoplastic binder material the applicator can be rendered flushable in conventional toilet systems. Coatings of different thermoplastics for the same applicator are also contemplated within the scope of this invention, and specific combinations of thermoplastics may be utilized for specific properties, e.g. surface finish, flushability, etc.

Suitable water dispersible and water soluble thermoplastic coatings are: polyethylene oxide, polyvinyl alcohol, polyvinyl acetate, polyvinyl pyrrolidone, and hydroxypropyl cellulose.

The concept of convolute winding is well known. Representative patent disclosing the concept is U.S. Pat. No. 2,518,075, issued to W. R. Schere. Further, the concept of using a thermoplastic as an adhesive to attach an added element, i.e., a finger griping ring is disclosed in U.S. Pat. No. 3,572,339 issued to Joseph A. Voss and Carl W. Johnson.

BRIEF SUMMARY OF THE INVENTION

According to this invention, a paper-based tampon tube is provided wherein a thermoplastic coating maintains the configuration of the tube, including its various shaped components, by heat setting. This invention also includes a process for making a paper-based tampon tube from a flat die-cut blank in which the tampon tube has arcuate lobes in a hemispherical configuration at its leading edge.

DETAILED DESCRIPTION OF THE INVENTION

The invention may more readily be understood by reference to the drawings in which.

Figure 1:
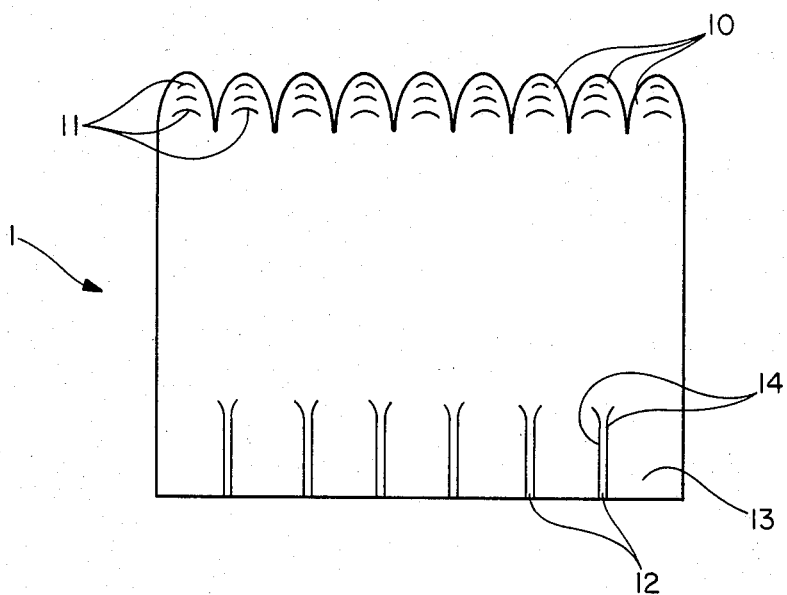
FIG. 1 is a plan view of the flat blank for the tampon tube of this invention.
Figure 2:
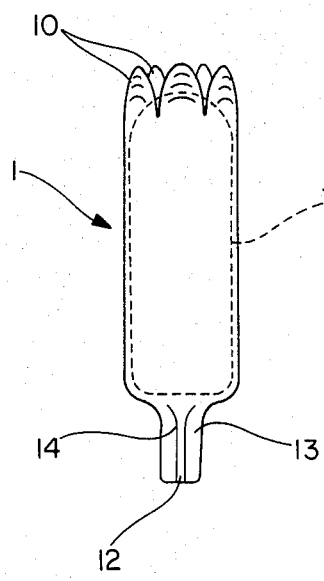
FIG. 2 is an end view of the tampon tube with the tampon inserted.

As can be seen in FIG. 1, a blank useful for making the tampon tube of this invention is formed by precutting the arcuate lobes 10 so that when the tampon tube is formed as shown in FIG. 2, the lobe configuration is already present at the leading or insertion edge. These lobes may be formed for example by die cutting. To provide increased flexibility, score lines 11 are preferably added during the forming process. The blank 1 also has score lines 14 present near the portion which will ultimately result in the necked in gripping area at the bottom of the tube. The score lines define a slightly recessed area 12 which can be formed by embossing. When the blank is rolled to form the tube as can be seen in FIG. 2 the surface of the compressed area 13 forms a sight of reduced diameter for positioning and gripping prior to insertion.

The blank may be made by laying several sheets of paper and attaching them by means of a heat settable adhesive or by a thermoplastic coating or, alternatively, it may be by a single thickened sheet of paper or cardboard or the like.

An outer surface of the blank can be coated or a coated paper may be used to provide the heat sensitive coating which is used for shape retention in the subject invention. The coating may be a polymer coating such as any of the common thermosensitive olefins like polypropylene or polyethylene or the coating may be in the form of a heat-activatable adhesive composition. The critical parameter for the coating is that it is flowable at temperatures below the charring or combustion temperature of paper and the melting point of common polyolefins are well known with the specific compositions useful in the practice of this invention not being part of the subject matter thereof.

The tampon tube is then formed as indicated in FIG. 2 and the coating activated by suitable heating means which may be dielectric, microwave, typical convection heating or the like. The heating source is withdrawn, the coating is set and the tube is formed with the coating as the means for maintaining its configuration. As can be seen in FIG. 2, partially in phantom lines, the tampon T is positioned within the tube and loaded from the leading edge. It is possible to load the tampon from the bottom if there is no reduced diameter gripping portion. The tampon may be inserted prior to heat setting or during heat setting depending upon the particular heat setting treatment desired. If heat setting is used which will not damage the surface of the pledget, it may be more convenient to insert the pledget prior to the heat activation and subsequent setting of the tube. This is particularly true because it would allow a single heating step for the setting of the tube configuration as well as the forming and positioning of the arcuate lobes about the leading edge of the tampon as will be discussed in more detail below.

The degree of winding will vary to some extent depending upon the thickness of the tube desired which is, of course, dependent upon the thickness of the blank. Another variable to take into account is the flexibility of the paper component after coating has been added because it is desirable that the tampon tube provide a smooth wrinkle free surface.

By convolutely winding, the arcuate lobes which will be eventually shaped in a hemispherical configuration can be positioned so that there is virtually no "ghosting". The perfect alignment of the convolutely wound lobes minimizes the potential for injury due to the overlap of the lobes between layers of paper.

The necked in portion can be formed at the bottom of the tube at the same time the tube is formed because of the compression associated with the areas 12 and 14 at the tube blank. When the slightly recessed area 12 and the scored lines 14 are formed in the manner depicted they can be easily compressed as the tube itself is convolutely wound.

Figure 3:
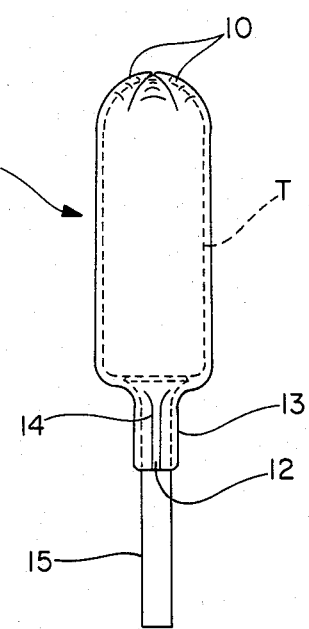
FIG. 3 is an end view of the tampon tube with the hemispherical forward end being formed.

As shown in FIG. 3, once the tampon is inserted, the lobes are inwardly bent against the hemispherical leading edge of the tampon and heat set. If heat setting of the tube forming step and the arcuate leading edge can be performed in the same operation, a substantial amount of energy and process time will be saved and this is indeed the preferred embodiment. There may be instances, however, when due to the choice of materials for the tampon itself or the paper this approach is undesirable.

As can also be seen from FIG. 3, a rod 15 which is preferably hollow extends into the interior portion of the tube and is designed to nest against the tampon T. When pressure is exerted against the rod 15, the tampon is dislodged and properly inserted. The score lines 11 help to increase the flexibility of the lobes 10 making the pressure required for such insertion minimal.

What is claimed is:

1. Convolutely wound flexible paper tampon tube designed to surround a tampon pledget with said tube having a hemispherical edge with a thermosensitive coating, a gripping end and insertion end; said insertion end comprising a plurality of nonoverlapping, multi-layered aligned arcuate lobes, each of said lobes scored near its base to increase flexibility, said lobes collectively deformable to form a hemispherical profile and cover said hemispherical leading edge of said tampon.

* * * * *